United States Patent
Danby et al.

Patent Number: 5,680,111
Date of Patent: *Oct. 21, 1997

[54] DUAL SENSOR AIR-IN-LINE DETECTOR

[75] Inventors: Hal C. Danby, Sudbury; Alan Keith Brundle, Halstead, both of United Kingdom

[73] Assignee: Baxter International Inc., Deerfield, Ill.

[*] Notice: The term of this patent shall not extend beyond the expiration date of Pat. No. 5,206,522.

[21] Appl. No.: 532,646
[22] PCT Filed: Feb. 3, 1995
[86] PCT No.: PCT/US95/01424
§ 371 Date: Sep. 22, 1995
§ 102(e) Date: Sep. 22, 1995
[87] PCT Pub. No.: WO95/21374
PCT Pub. Date: Aug. 10, 1995

[30] Foreign Application Priority Data

Feb. 5, 1994 [GB] United Kingdom ............... 9402256

[51] Int. Cl.$^6$ ...................................... G08B 17/10
[52] U.S. Cl. ............ 340/632; 340/627; 250/573; 250/574; 250/575; 250/576
[58] Field of Search ............ 340/632, 627; 250/573, 574, 576, 575; 356/338, 339, 343, 222

[56] References Cited

U.S. PATENT DOCUMENTS

| | | | |
|---|---|---|---|
| 3,544,798 | 12/1970 | Topol | 250/573 |
| 4,227,814 | 10/1980 | Soodak et al. | 356/410 |
| 4,319,138 | 3/1982 | Sweet | 250/576 |
| 4,366,384 | 12/1982 | Jensen | 250/575 |
| 4,857,050 | 8/1989 | Lentz et al. | 604/67 |
| 4,884,065 | 11/1989 | Crouse et al. | 340/632 |
| 5,102,392 | 4/1992 | Sakai et al. | 604/42 |
| 5,206,522 | 4/1993 | Danby et al. | 250/574 |

FOREIGN PATENT DOCUMENTS

| | | |
|---|---|---|
| 0050812 | 5/1982 | European Pat. Off. . |
| 0121848 | 10/1984 | European Pat. Off. . |
| 0199919 | 11/1986 | European Pat. Off. . |
| 0209659 | 1/1987 | European Pat. Off. . |
| 0238809 | 9/1987 | European Pat. Off. . |
| 0289833 | 11/1988 | European Pat. Off. . |
| 1254708 | 11/1971 | United Kingdom . |

*Primary Examiner*—Jeffery Hofsass
*Assistant Examiner*—Julie B. Lieu
*Attorney, Agent, or Firm*—Francis C. Kowalik

[57] ABSTRACT

A device for the reliable detection of air or air bubbles in transparent or translucent tubing carrying a fluid which includes a transmitter element for transmitting a light beam to the fluid contained in a large-bore thin-walled transparent tubing, and a pair of first and second light receiver devices for receiving reflected and transmitted light emitted from the transmitter element and which is incident upon the fluid conducting tubing. The light transmitter and receivers are located within a body member around the fluid conducting tubing. Also, an acrylic optical spacer which has a passage for accommodating the tubing is located within the body member. One light receiver is disposed at a 90° angle in relation to the optical axis of the transmitter, while the other receiver is arranged at a 180° angle. Outputs of the light receivers are applied to a processor, which processes the light receivers outputs to detect air in the tubing.

15 Claims, 6 Drawing Sheets

DUAL SENSOR AIR-IN-LINE DETECTOR

FIELD OF THE INVENTION

This invention relates to devices for detecting gas, e.g. air or air bubbles, in fluid conducting tubing and in particular in fluid conducting tubing forming part of a fluid flow system utilized for the intravenous supply of fluid to a medical patient.

DISCUSSION OF BACKGROUND

Typically transparent walled p.v.c. tubing is employed in systems as last-mentioned because it is hygienic and cheap it being common practice to change and discard the length of tubing in use frequently. A known arrangement for use in clinical analysis and capable of detecting air in tubing utilizes a device as illustrated in transverse section in FIG. 1 of the accompanying drawings.

Referring to FIG. 1, the known device includes a body member 1 having a passage 2 passing therethrough in which may be accommodated a length of transparent walled p.v.c. tubing 3. Passage 2 is open at the top (as viewed) in order that the tubing 3 may readily be slotted into position and of course removed after use. Extending into the body 1 from its base and right-hand side (as viewed) respectively are two circular-cylindrical passages 4 and 5 which are orthogonal to each other and exit via apertures 6, 7 respectively into tubing passage 2. Located in circular cylindrical passage 4 is an infra-red receiver 8 (a phototransistor) which receives infra-red energy transmitted by an infra-red transmitter 9 (an LED).

In operation the output level of receiver 8 depends upon the nature of the fluid passing through the tubing 3 past receiver 8 and transmitter 9. Different fluids will result in different output levels with a significant change if a gas, e.g. air, is present. For example, in a test a voltmeter 10 connected to the output of a suitable detector circuit 11 was found to indicate 0.1 volts when the fluid passing through tubing 3 was distilled water; 0.2 volts when the fluid was semi-skimmed milk; 1.4 volts when the fluid was a 20% intralipid solution and 4.2 volts when air passed through.

While not a primary function of a clinical analyzer, a device as shown in FIG. 1 will therefore operate as a detector of air passing through tubing 3. However, as is represented, p.v.c. tubing typically used in a clinical analyzer is small bore thick-walled tubing with an outside diameter of 2.5 mm and an inside diameter of 0.9 mm. In the intravenous supply of fluids to a patient however, the standard p.v.c. tubing used is of relatively large bore and thin walled having an outside diameter of 4 mm and an inside diameter of 3.1 mm.

Experiments have been carried out in connection with the detection of air-in-line with a device generally as illustrated in FIG. 1, but adapted dimensionally to accept the relatively large bore, thin wailed tubing utilized for the intravenous supply of fluid to a patient but the results achieved were not satisfactory. Particularly bearing in mind the critical importance of detecting "air-in-line" in such applications, the changes that took place in the output of the receiver corresponding to receiver 8 in FIG. 1 were insufficiently marked for the device to be regarded as useful in this connection. However, further experimentation led to the introduction of an optical spacer between the transmitter and the tubing, and the tubing and the receiver and with this, markedly improved results were achieved.

Such an optical spacer is known from EP-A-0481656, which discloses a device for detecting the presence of air in liquid conducting, translucent or transparent tubing, the device comprising a passage for accommodating of said tubing, a transmitter for transmitting radiation (in this case, light) towards said passage; a receiver for receiving radiation from said passage which has passed through the tubing, the receiver being operable to produce an output signal (i) when air is present in the tubing and/or (ii) when the dilution ratio of the liquid in the tubing is below a first predetermined threshold; and processing means. The processing means processes said output signal to provide an indication that air is present in the tubing. Hence, the device tends to make a false detection that air is present in instances defined in (ii) above.

Claim 1 relates to an improvement of the device of EP-A-0481656, wherein the improvement comprises means for eliminating false detections made by the receiver, that gas is present in the tubing, and comprising means (iii) a second receiver for receiving from said passage radiation which has passed through said tubing, the second receiver being operable to produce an output signal when gas is present in the tubing, the second receiver making false detections under different liquid conditions from the first receiver, and (iv) processing means operatively connected to both receivers to receive said output signals to provide an indication that gas is present in the tubing only when the output signals from both receivers are present.

Preferably the transmitter and receivers are respectively a light energy transmitter and light energy receivers and are all operative in the infra-red spectrum, and preferably the transmitter is a LED (light emitting diode) and the receivers are phototransistors.

Preferably, the device includes an optical spacer defining said passage and occupying space between said passage and said transmitter and between said passage and said receivers, the optical spacer comprising a cylindrical element having a dielectric constant greater than that of air, said tubing passage extending along a longitudinal axis of the cylindrical element for accommodating said tubing in intimate contact with said cylindrical element.

Preferably, the optical spacer is in the form of a collar surrounding the tubing, the transmitter and the receivers being housed in the body. Preferably the transmitter and the receivers are located in passages extending through the body and opening towards the tubing accommodating passage.

Normally the transmitter and receiver locating passages open towards the tubing accommodating passage via respective apertures. The apertures may be in fixed walls, integral with the body, which otherwise close the passages or in plugs inserted in the passages otherwise to close the same.

The apertures may be of different sizes chosen to provide optimum effect in any given device. Commonly, the aperture through which the transmitter communicates will be of smaller cross-sectional area than the apertures through which the receivers communicate. In one embodiment wherein the apertures are of circular cross-section, the diameter of the aperture through which the transmitter communicates is at least approximately half the diameter of the apertures through which the receivers communicate.

Preferably the transmitter and receivers are spaced around the tubing accommodating passage, preferably with their principle optical axis in the same transverse plane. Preferably again the receivers are arranged with their principle optic axes orthogonal one to the other. Where the axes lie in the same transverse plane it may be found that satisfactory results are obtained with the optic axes at some relative angle other than 90° but it is believed that optimum results are obtained when the axes are orthogonal one to the other. Again, spacing the transmitter and receivers along the length of the tubing accommodating passage may be found to give satisfactory results but arranging the transmitter and receivers such that their principle optic axes are spaced around the tubing accommodating passage is believed to provide optimum results. The tubing used in the intravenous supply of fluids to a patient is of course of circular cross-section and therefore for this application the tubing accommodating passage is normally of circular cross-section.

Typically the outer diameter of the optical spacer, when present, will be between twice and three times the outside diameter of said tubing. In a preferred embodiment the outer diameter of the spacer is 2.5 times the outer diameter of the tubing. Preferably the transmitter and receivers are discrete devices and preferably an LED (light emitting diode) and phototransistors, respectively. Normally such components are generally circular-cylindrical in overall outline and accordingly, the transmitter and receiver passages are normally circularly cylindrical. In order to simplify the insertion and removal of the tubing, preferably the tubing accommodating passage has a linearly extending slot through which the tubing may be slotted.

The material chosen for the optical spacer, when present, should have a dielectric constant which is an optically reasonable match to the material of said tubing. Preferably the material is acrylic.

In a preferred embodiment, the transmitter projects a light beam to the fluid conducting tube and light receivers in the form of a pair of sensors disposed perpendicularly to each other operate in opposite modes such that if an air bubble is present in the line the detector will be able to reliably distinguish this situation from the case where there is no air bubble. One sensor is disposed 90° from the optical axis of the transmitter, while the other sensor is disposed 180°, ie., along the transmitter optical axis. Light beams projected from the transmitter are incident on the tubing and are thus reflected or transmitted depending upon the characteristics of the fluid (eg., the opacity of the fluid and/or dilution ratio of the fluid) and also upon the presence or absence of air or air bubbles in the line. The two perpendicularly disposed sensors provide outputs indicative of the amount of light received. A processor determines the presence or absence of air in the line based on the combination of the outputs of the two sensors. When the outputs of both sensors are high, the processor determines that air is present in the line, whereas if one of the two sensors' outputs is low, the processing device determines that no air is present in the line. With this arrangement, both sensor outputs are used in order to determine the presence or absence of air or air bubbles in the fluid conducting tubing, thus providing a reliable detection apparatus regardless of the initial calibration of the sensors and transmitter.

DESCRIPTION OF THE PREFERRED EMBODIMENTS

Figure 2:
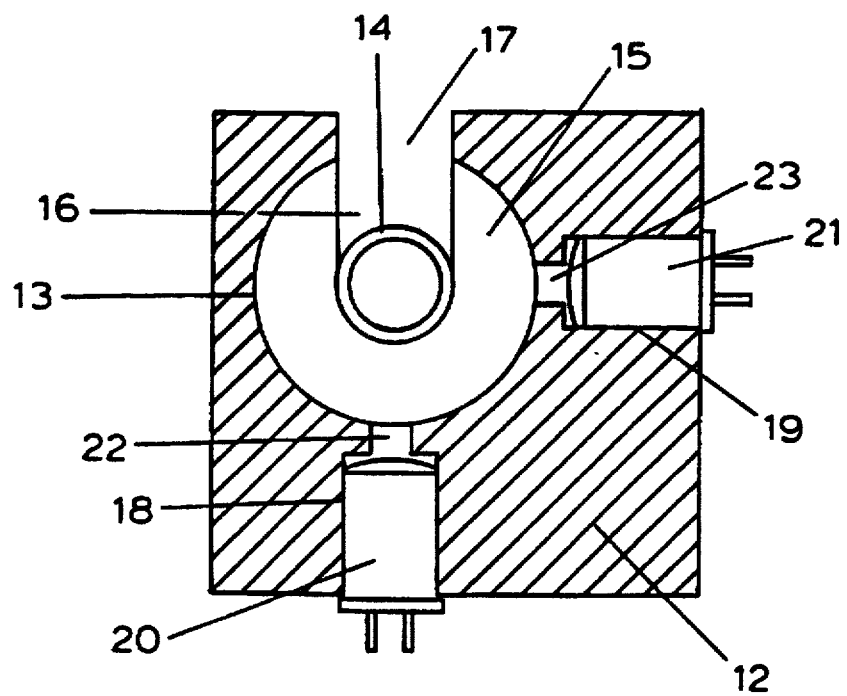
FIG. 2 is a transverse cross-sectional view of the device disclosed in EP-A-0481656 for detecting the presence of air in tubing forming part of a fluid flow system for the intravenous supply of fluid to a medical patient.

Referring now to the drawings, wherein like reference numerals designate identical or corresponding parts throughout the several views, and more particularly to FIG. 2 thereof, a device as disclosed in EP-A-0481656 includes a body member 12 having a tubing accommodating passage 13 passing therethrough in which may be accommodated a length of transparent large bore thin-walled p.v.c. tubing 14. Tubing 14 has an internal diameter of 3.0 mm and an outside diameter of 4.1 mm. Passage 13 preferably has a diameter equal to 10 mm. Located within passage 13 is an optical spacer 15 of material chosen to be a good optical match with the material of the tubing 14. In this case the material of the optical spacer 15 is acrylic. The optical spacer 15 surrounds the tubing 14 save for a gap 16 which is of width sufficient for the tubing 14 to pass through. Gap 16 is aligned with a slot 17, of similar width, extending longitudinally through the top (as viewed) of the passage 13. The slot 17 and gap 16 enable the tubing 14 to be readily slotted into position and removed after use. Extending into the body 12 from its base and right-hand side (as viewed) respectively are two circular-cylindrical passages 18 and 19 in which are located respectively an infra-red receiver 20 in the form of a phototransistor and an infra-red transmitter 21 in the form of an LED. Circular-cylindrical passages 18, 19 are orthogonal to each other and exit via apertures 22, 23, respectively, into tubing accommodating passage 13. The openings of apertures 22, 23 in passage 13 are covered by the outer surface of optical spacer 15. In this particular example the receiver and transmitter apertures 22, 23 are not of the same diameter. The diameter of transmitter aperture 23 is one-half that of receiver aperture 22.

Figure 1:
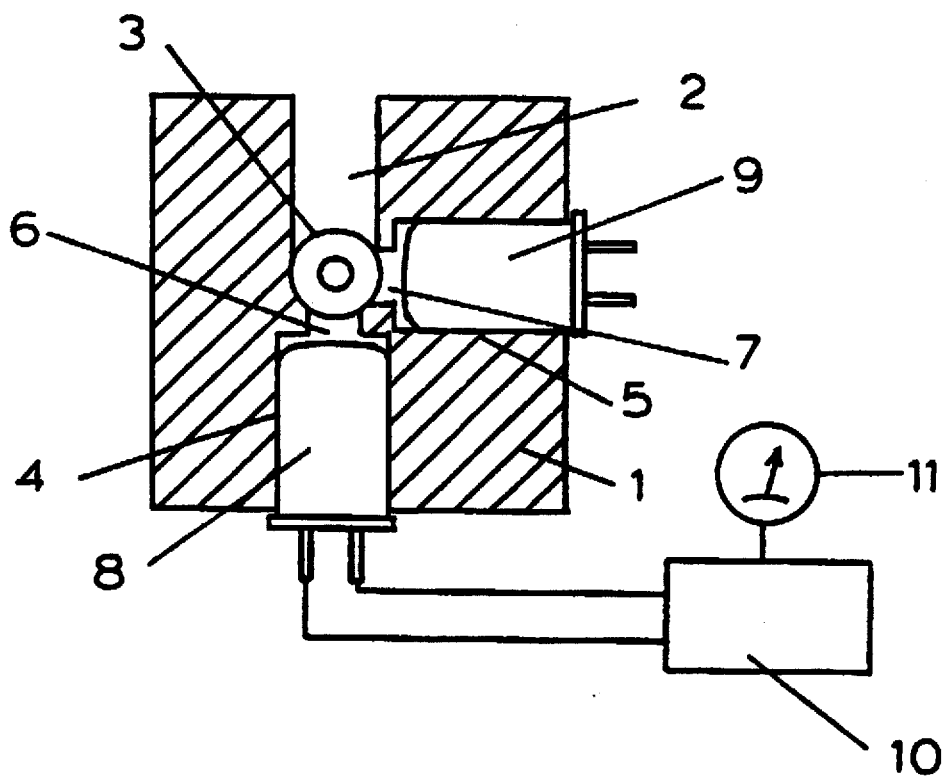
FIG. 1 is a cross-sectional view of a conventional device for detecting air in tubing.

With an arrangement as described above and utilizing for infra-red transmitter 21 a type TSTS 7202 LED and for infra-red receiver 20 a type BPW 77B and with receiver and transmitter apertures of diameter 3.0 mm and 1.5 mm respectively, a test corresponding to that described earlier in reference to FIG. 1 provided an indication of 0.3 volts when the fluid passage through tubing 14 was distilled water; 1.2 volts when the fluid was semi-skimmed milk; 1.2 volts when the fluid was 20% intralipid solution and 4.0 volts when air passed through. It will be recalled that with an arrangement generally as illustrated in FIG. 1 (but adapted dimensionally to accept relatively large bore, thin-walled tubing such as tubing 14 in FIG. 2, in contrast) provided a change in output in the presence of air which was insufficiently marked to be useful in the terms of "air-in-line" detection.

Figure 3:
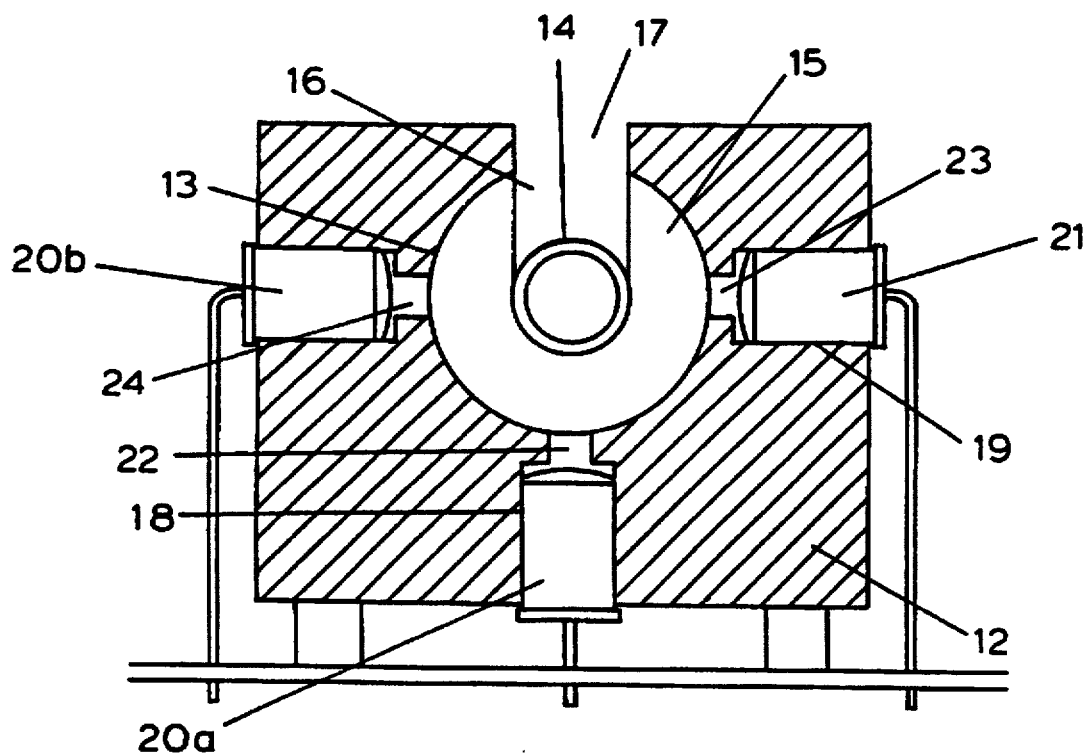
FIG. 3 shows an arrangement of an embodiment according to the present invention wherein a single transmitter and a pair of sensors which are provided perpendicularly to each other are shown.

An embodiment of the present invention will now be described with reference to FIG. 3 of the accompanying drawings. In this embodiment an additional sensor 20b is provided along the longitudinal axis of transmitter 21 at a 90° angle to sensor 20a. As shown in FIG. 3, infrared LED transmitter 21 of type TS 7302, for example, is provided for projecting a beam of light to fluid conducting tubing 14. The phototransistors 20a, 20b of type BPW 77, for example, also operate in the infrared spectrum wherein sensor 20a is provided at a right angle to the direction of incidence of the light beam from the transmitter, while sensor 20b is provided along a path parallel to the direction of light beam incidence, ie., at a 180° angle. A transparent optical spacer 15 which may be of acrylic material, for example, is also provided within a tubing accommodating passage 13 in the body member 12 for holding the large-bore thin-walled tubing 14.

The transmitter and first and second energy receivers are located in respective passages which extend through the body member and open into the tubing accommodating passage. Apertures 22, 23, 24 are shown which connect the tubing accommodating passage with each of the respective passages provided for the transmitter and receivers. The apertures may be of different sizes for each of the receivers and transmitter or, alternatively, may be the same size for two of these elements and of a different size for the third element. Also, the transmitter aperture may be of smaller cross-sectional area than the aperture through which light is received by the first and second receivers. In a preferred embodiment, the apertures are of circular cross-section with the diameter of the aperture through which the transmitter transmits light being approximately 1.5 times greater than the diameter of the apertures through which the first and second receivers communicate with the tubing accommodating passage. However, the invention is not limited to such a circular cross-sectional shape for the apertures. A suitable diameter for the optical spacer is between 2 and 3 times larger than the outer diameter of the large-bore thin-walled tubing. A preferred outer diameter of the tubing accommodating passage is approximately 2.5 times greater than the outer diameter of the tubing.

Figure 4:
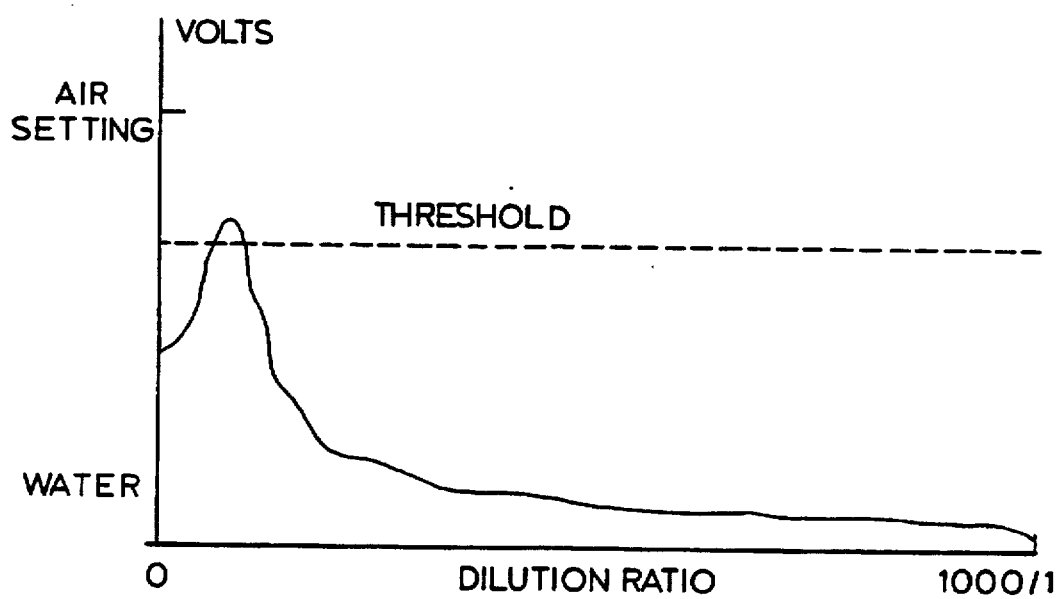
FIG. 4 illustrates the output of sensor 20a shown in FIG. 3.
Figure 5:
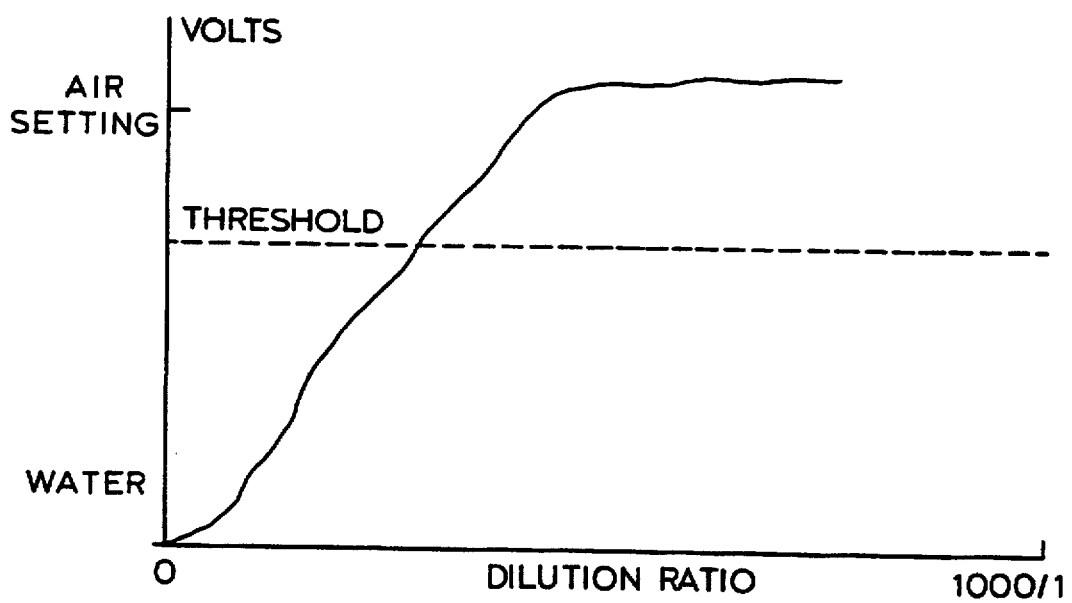
FIG. 5 shows the output of sensor 20b shown in FIG. 3.

With the arrangement of the transmitter and sensors shown in FIG. 3, the voltage outputs provided by sensors 20a and 20b are as shown in FIGS. 4 and 5. As discussed above, using the output of sensor 20a alone will provide satisfactory results provided that the calibration of the transmitter and sensor is within a predetermined range. However, as shown in the "worst case" calibration illustrated in FIG. 7, the output of sensor 20a at a dilution ration of 9/1 for a 20% intralipid solution may be equal to the calibrated output of sensor 20a, ie., the air setting value. Since this air setting value may be the same as the output when an air bubble is present in the line, the device shown in FIG. 2 of the drawings (which only uses sensor 20) will be unable to distinguish between the presence of an air bubble in the line and the case where no air bubble is present. With the device illustrated in FIG. 3, on the other hand, even in the "worst case" calibration situation, the detector will be able to distinguish between an air bubble and the absence of an air bubble at any dilution ratio due to the use of the second sensor 20b which operates in an opposite mode from that of sensor 20a. In other words, at low dilution ratios such as approximately 10/1, for example, the output of sensor 20b will be low, when the output of sensor 20a is high. Similarly, when the dilution ratio is high, the output or sensor 20b will be high while the output of sensor 20a will be low.

It is important to note that for either sensor when an air bubble is present in the line the output of each of the sensors will be high, ie., will be equal to the air setting or calibration value. Thus for the situation when an air bubble is present in the line and the dilution ratio is such that the output of sensor 20a is substantially equal to the output of sensor 20a for the case when an air bubble is present, the output of sensor 20b will also be high (3 volts) and equal to the air setting value. In this manner, the detector device according to the present invention will be able to reliably detect when an air bubble is in fact present in the fluid conducting tubing. On the other hand, if no air bubble or bubbles are present, the output of sensor 20a may be high but the output of sensor 20b will be low, thereby indicating that no air bubbles are present.

The results of the experimental data are shown in the following table.

TABLE 1

| Dilution | Worst Case Sensor 20a | Sensor 20b | Best Case Sensor 20a | Sensor 20b |
| --- | --- | --- | --- | --- |
| Intra 100% | 2.04 | 0.01 | 1.27 | 0.01 |
| 2:1 | 2.61 | 0.02 | 1.87 | 0.02 |
| 4:1 | 3.87 | 0.14 | 2.44 | 0.04 |
| 8:1 | 4.15 | 0.01 | 2.70 | 0.1 |
| 10:1 | 3.16 | 0.24 | 2.57 | 0.15 |
| 16:1 | 3.99 | 0.07 | 2.53 | 0.12 |
| 20:1 | 3.55 | 0.18 | 2.20 | 0.22 |
| 30:1 | 2.34 | 0.52 | 1.73 | 0.41 |
| 40:1 | 2.34 | 0.48 | 1.55 | 0.57 |
| 50:1 | 1.95 | 0.62 | 1.30 | 0.82 |
| 60:1 | 1.81 | 0.74 | 1.37 | 0.65 |
| 70:1 | 1.55 | 0.97 | 1.13 | 0.84 |
| 80:1 | 1.30 | 1.30 | 1.08 | 0.91 |
| 90:1 | 1.10 | 1.60 | 0.87 | 1.25 |
| 100:1 | 0.99 | 2.00 | 0.70 | 1.90 |
| 500:1 | 0.68 | 4.74 | 0.46 | 4.71 |
| 1000:1 | 0.58 | 4.76 | 0.48 | 4.77 |

Figure 6:
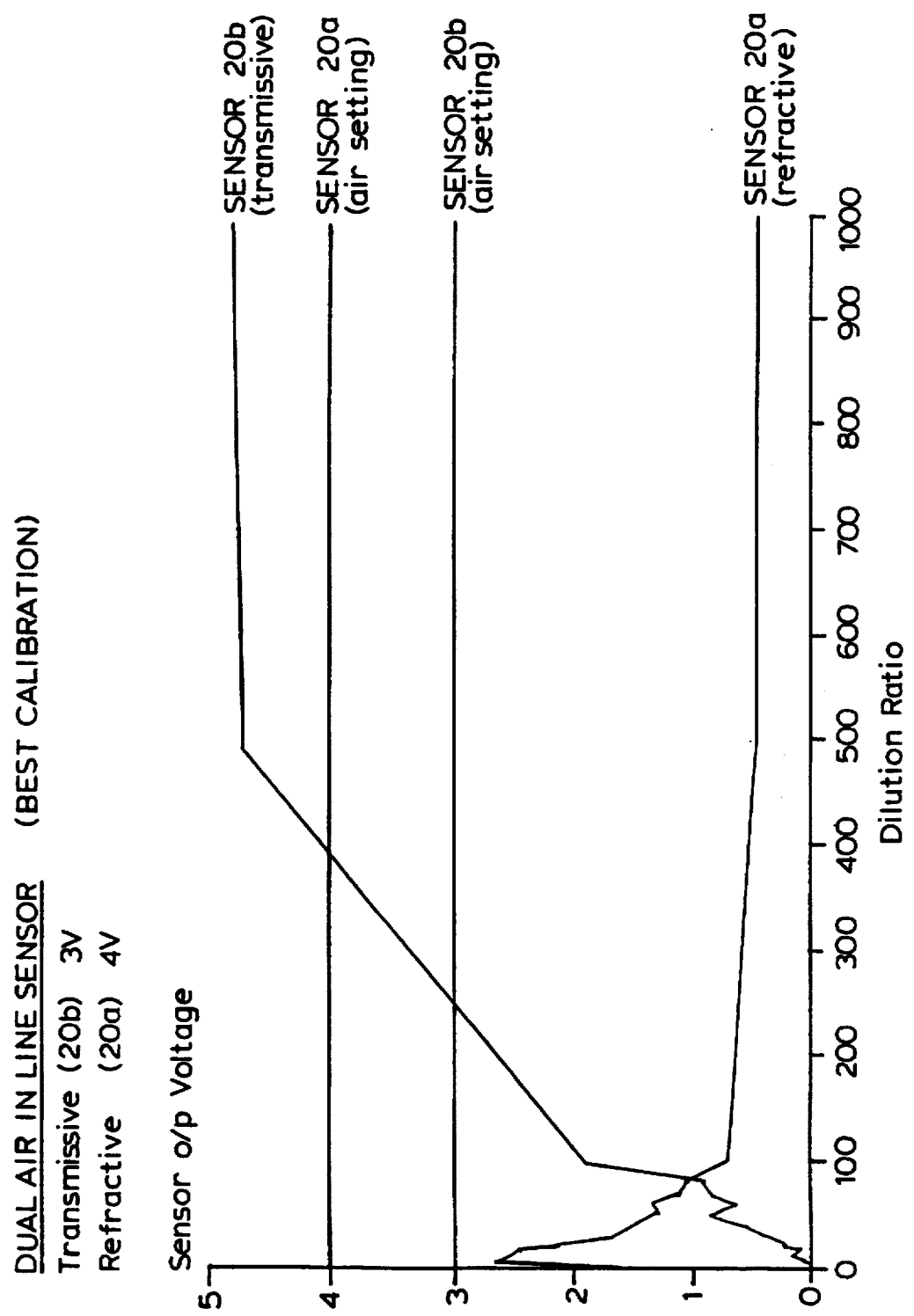
FIG. 6 illustrates a graph of the values shown in Table 1 for a "best calibration" case.
Figure 7:
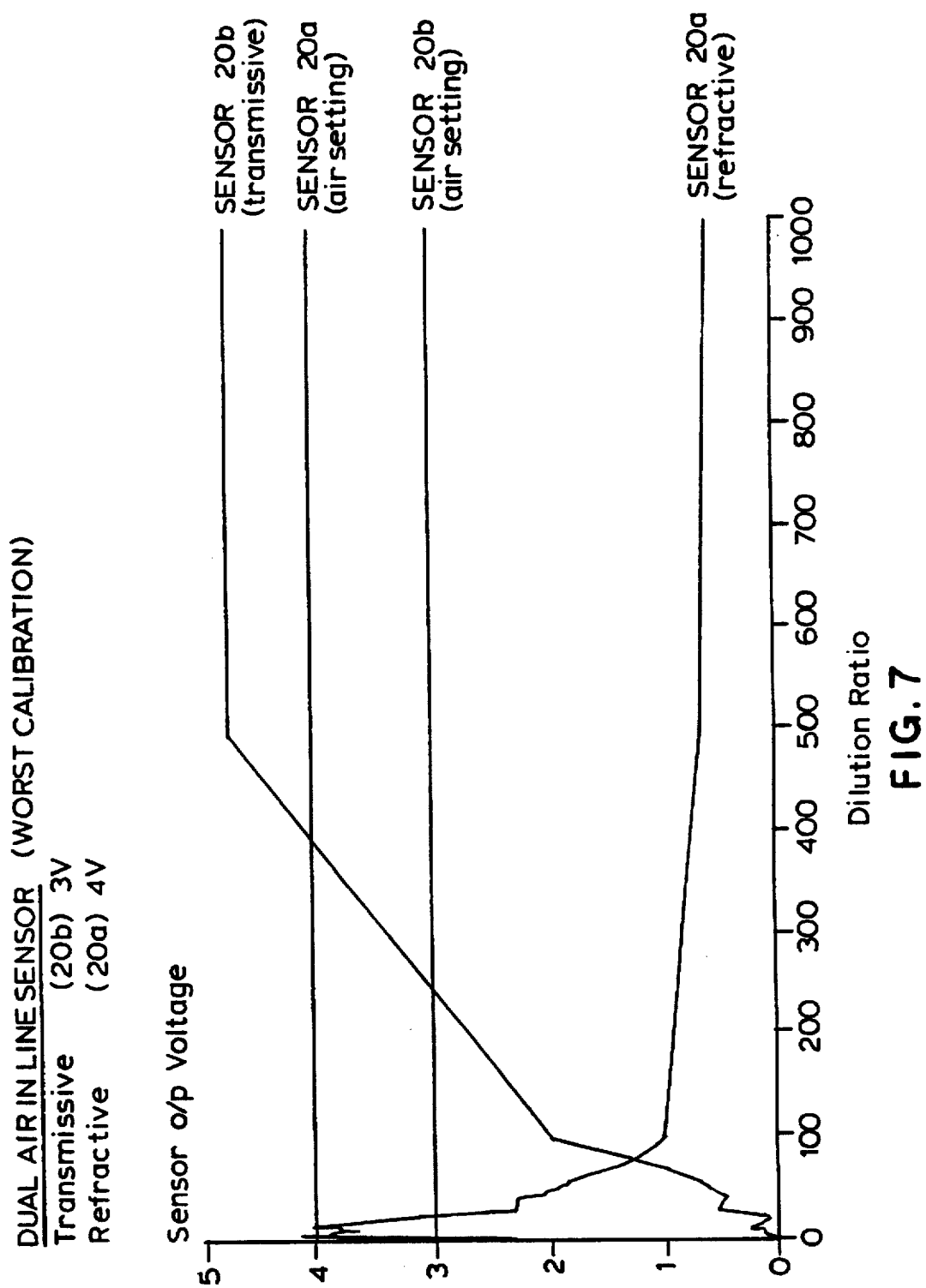
FIG. 7 is a graph of the values of Table 1 for the "worst case" calibration.

The results of the preceding Table 1 are illustrated graphically in FIGS. 6 and 7 of the accompanying drawings. FIG. 6 shows the best calibration results, ie., the calibration of output sensors such that the output of sensor 20a does not intersect the output of sensor 20a for an air setting, ie., 4.0 volts. However, as shown in FIG. 7, for worst case calibration the output of sensor 20a at relatively low dilution ratios may be the same as the output of sensor 20a for the air setting case, and also the case when an air bubble is present in the fluid line. However, using the two sensors together, the situation when no air bubble is present can be easily determined since the output of sensor 20b will be low at the point where the output of sensor 20a is close to the air setting value. If, on the other hand, an air bubble is present in the line, both sensors 20a and 20b will indicate high outputs which will never be the case when air is not present in the line. The results can be summarized in the following table.

TABLE 2

| FLUID | SENSOR 20a | SENSOR 20b |
| --- | --- | --- |
| Air | High | High |
| Water | Low | High |
| Dense Fluid | Low or High | Low |

Figure 8:
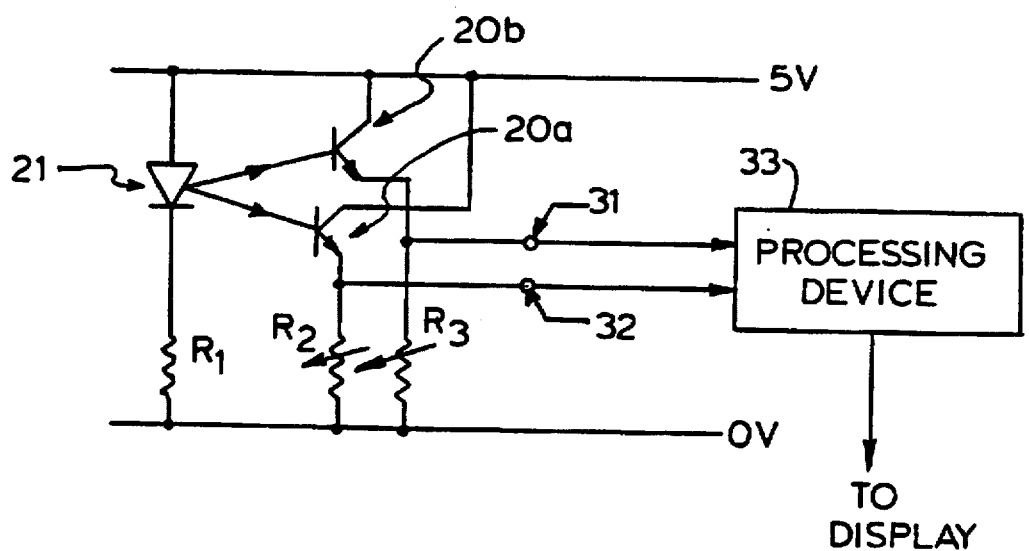
FIG. 8 is a circuit diagram illustrating the relationship between the transmitter and sensors of FIG. 3.

FIG. 8 illustrates the circuit diagram arrangement of the transmitter and sensors of FIG. 3. As shown, the transmitter 21 is connected in series with a resistor $R_1$ equal to 100 ohms in a preferred embodiment, and is connected between a 5 volt source and ground. Also, it should be noted that the angle between the light beams received by sensor 20a and those received by sensor 20b is equal to 90° since the sensors are at right angles to each other, and thus the angle illustrated in FIG. 8 is not to be considered the actual angle between sensors 20a and 20b. Output terminals 32, 31 of sensors 20a, 20b respectively, are connected to ground through 200 KΩ variable resistors $R_2$, $R_3$, respectively. The outputs of sensors 20a, 20b are input to a processing device 33 which determines the presence or absence of air in the tubing 14 and outputs appropriate signals to a display device (now shown). Processing device 33 outputs a first signal when the outputs of sensors 20a and 20b are both high, a second signal when the output of sensor 20a is low and sensor 20b is high (indicating water or a highly low diluted solution), and a third signal whenever the output of sensor 20b is low (indicating a dense fluid at low dilution). The processing device 33 may include a microprocessor operating under program control for generating the appropriate output signals corresponding to the outputs received from the sensors 20a, 20b thereby indicating the presence or absence of air in the line. Alternatively, the processing device 33 may include discrete logic circuits for receiving the outputs of the light receivers and generating the requisite outputs.

We claim:

1. In a device for detecting and indicating the presence of gas in liquid conducting tubing, the device comprising a member defining a passage for accommodating tubing; a transmitter for transmitting radiation towards said passage; and a receiver for receiving from said passage radiation which has passed through said tubing, the receiver being operable to produce an output signal when gas is present in the tubing, the improvement comprising means for eliminating false detections made by said receiver that gas is present in the tubing length and comprising:

(i) a second receiver for receiving from said passage, radiation which has passed through said tubing, the second receiver being operable to produce an output signal when gas is present in the tubing, the second receiver making false detections under different liquid conditions from the first receiver, and (ii) Processing means operatively connected to both receivers to receive said output signals to provide an indication that gas is present in the tubing only when the output signals from both receivers are present; and (iii) an optical spacer defining said passage and occupying space between said passage and said transmitter and between said passage and said receivers, the optical spacer comprising a cylindrical element having a dielectric constant greater than that of air, said tubing passage extending along a longitudinal axis of the cylindrical element for accommodating said tubing in intimate contact with said cylindrical element; and (iv) said transmitter and said first and second receivers are operative in the infrared spectrum.

2. The device according to claim 1, wherein the principle optical axis of said transmitter and said first and second receivers intersect the axis of said passage and are in a common transverse plane.

3. The device according to claim 1, wherein said first and second receivers are mounted in said device substantially perpendicular to each other.

4. The device according to claim 3, wherein said transmitter is mounted perpendicularly to said first receiver and along the optical axis of said second receiver so as to be facing said second receiver.

5. The device according to claim 1, wherein said transmitter and said first and second receivers are operative in the infrared spectrum.

6. The device according to claim 1, wherein said transmitter comprises an LED and said first and second receivers comprise phototransistors.

7. An apparatus for supplying a medical fluid to a patient, comprising tubing having a portion thereof mounted in the passage of a device according to claim 1, wherein each receiver is operable to produce an output signal when air is present in said portion of the tubing.

8. A device for detecting and indicating the presence of gas in liquid conducting tubing, the device comprising a member defining a passage for accommodating tubing;

a transmitter for transmitting radiation towards said passage;

a first receiver for receiving from said passage radiation which has passed through said tubing, the first receiver being operable to produce an output signal when gas is present in the tubing and making false detections that gas is present in the tubing under first liquid conditions a second receiver for receiving from said passage radiation which has passed through said tubing, the second receiver being operable to produce an output signal when gas is present in the tubing and making false detections under different liquid conditions from the first liquid conditions;

processing means operatively connected to both receivers to receive said output signals to provide an indication that gas is present in the tubing only when the output signals from both receivers are present and an optical spacer defining said passage and occupying space between said passage and said transmitter, and between said passage and said receivers, the optical spacer comprising a cylindrical element having a dielectric constant greater than that of air, said tubing passage extending along a longitudinal axis of the cylindrical element for accommodating said tubing in intimate contact with said cylindrical element.

9. The device according to claim 8, wherein the principle optical axis of said transmitter and said first and second receivers intersect the axis of said passage and are in a common transverse plane.

10. The device according to claim 8, wherein said first and second receivers are mounted in said device substantially perpendicular to each other.

11. The device according to claim 10, wherein said transmitter is mounted perpendicular to said first receiver and along the optical axis of said second receiver so as to be facing said second receiver.

12. The device according to claim 8, wherein said transmitter and said first and second receivers are operative in the infrared spectrum.

13. The device according to claim 8, wherein said transmitter comprises and LED and said first and second receivers comprise phototransistors.

14. An apparatus for supplying a medical fluid to a patient, comprising tubing having a portion thereof mounted in the passage of a device according to claim 8, wherein each receiver is operable to produce an output signal when air is present in said portion of the tubing.

15. A device for detecting and indicating the presence of air in liquid conducting tubing, the device comprising:

a member defining a passage for accommodating tubing;

a transmitter for transmitting light towards said passage;

a receiver for receiving from said passage light which has passed through said tubing, the receiver being operable to produce an output signal when (a) air is present in the tubing and/or (b) when the dilution ratio of the liquid in the tubing is below a first predetermined threshold;

a second receiver for receiving from said passage light which has passed through said tubing, the second receiver being operable to produce an output signal when (c) air is present in the tubing and/or (d) when the dilution ratio of the liquid in the tubing is above a second predetermined threshold; and processing means operatively connected to both receivers to receive said output signals to provide an indication that air is present in the tubing only when the output signals from both receivers are present; and an optical spacer defining said passage and occupying space between said passage and said transmitter, and between said passage and said receivers, the optical spacer comprising a cylindrical element having a dielectric constant greater than that of air, said tubing passage extending along a longitudinal axis of the cylindrical element from accommodating said tubing in intimate contact with said cylindrical element.

* * * * *